(12) United States Patent
Quaranta et al.

(10) Patent No.: US 8,440,595 B2
(45) Date of Patent: May 14, 2013

(54) FUNGICIDES

(75) Inventors: Laura Quaranta, Stein (CH); Fiona Murphy Kessabi, Stein (CH); Renaud Beaudegnies, Stein (CH); Hans-Georg Brunner, Lausen (CH); Fredrik Cederbaum, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 312 days.

(21) Appl. No.: 12/676,702

(22) PCT Filed: Sep. 3, 2008

(86) PCT No.: PCT/EP2008/007196
§ 371 (c)(1),
(2), (4) Date: Jul. 20, 2010

(87) PCT Pub. No.: WO2009/049716
PCT Pub. Date: Apr. 23, 2009

(65) Prior Publication Data
US 2010/0286199 A1    Nov. 11, 2010

(30) Foreign Application Priority Data

Sep. 5, 2007 (GB) .................................. 0717260.4

(51) Int. Cl.
*C07D 215/38*    (2006.01)

(52) U.S. Cl.
USPC ........... 504/247; 546/159; 546/161; 546/162; 546/163

(58) Field of Classification Search ............... 546/159, 546/161, 162, 163; 504/247
See application file for complete search history.

(56) References Cited

U.S. PATENT DOCUMENTS

| | | | |
|---|---|---|---|
| 7,956,188 B2 * | 6/2011 | Salmon et al. | 546/159 |
| 8,067,592 B2 * | 11/2011 | Crowley et al. | 544/283 |
| 2010/0056570 A1 * | 3/2010 | Murphy et al. | 514/314 |
| 2010/0256183 A1 * | 10/2010 | Beaudegnies et al. | 514/311 |

FOREIGN PATENT DOCUMENTS

| WO | 2004108663 | * 12/2004 |
|---|---|---|
| WO | 2006058700 | * 6/2006 |

* cited by examiner

*Primary Examiner* — D M Seaman
(74) *Attorney, Agent, or Firm* — R. Kody Jones

(57) ABSTRACT

Fungicidal compounds of the general formula (I), wherein the substituents are as defined in claim 1.

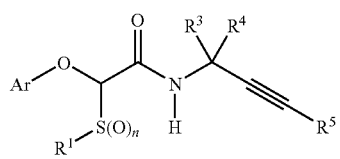

(1)

15 Claims, No Drawings

FUNGICIDES

This application is a 371 of International Application No. PCT/EP2008/007196 filed Sep. 3, 2008, which claims priority to EP 0717260.4 filed Sep. 5, 2007, the contents of which are incorporated herein by reference.

This invention relates to novel N-alkynyl-2-alkylthio-2-(substituted heteroaryloxy)-alkylamides and to their sulphinyl and sulphonyl derivatives. It also relates to processes for preparing them, to compositions containing them and to methods of using them to combat fungi, especially fungal infections of plants.

Certain N-alkynyl-2-alkylthio-2-(substituted heteroaryloxy)alkylamides and their sulphinyl and sulphonyl derivatives are described, for example, in WO 04/108663 as being useful as fungicides.

The present invention is concerned with the provision of new N-alkynyl-2-alkylthio-2-(iodo-substituted heteroaryloxy)alkylamides and their sulphinyl and sulphonyl derivatives with improved properties as plant fungicides.

Thus, according to the present invention there is provided a compound of the general formula (1):

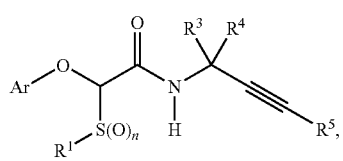

wherein Ar is a group of the formula (A):

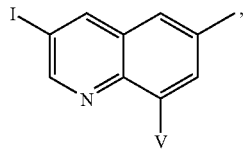

wherein
V is H, halogen or methyl,
$R^1$ is methyl or ethyl,
$R^3$ and $R^4$ are independently H, $C_{1-3}$ alkyl, $C_{2-3}$ alkenyl or $C_{2-3}$ alkynyl, or
$R^3$ and $R^4$ join with the carbon atom to which they are attached to form a 4 or 5-membered carbocyclic ring optionally containing one O, S or N atom and optionally substituted with halogen or $C_{1-4}$ alkyl,
$R^5$ is H, $C_{1-4}$ alkyl or $C_{3-6}$ cycloalkyl or $C_{3-6}$ cycloalkoxy or $C_{2-4}$ alkenyl, in which the alkyl or cycloalkyl or cycloalkoxy or alkenyl group is optionally substituted with halogen, hydroxy, $C_{1-6}$ alkoxy, $C_{1-4}$ alkoxy-$C_{1-4}$ alkoxy, cyano, $C_{3-6}$ alkenyloxy or $C_{3-6}$ alkynyloxy, and
n is 0, 1 or 2.

For the avoidance of doubt, the unattached single bond shown in the group of formula (A) indicates the point of attachment of the Ar group in the compound of formula (1) to the rest of the molecule.

The compounds of the invention contain at least one asymmetric carbon atom (and at least two when $R^3$ and $R^4$ are different) and may exist as enantiomers (or as pairs of diastereoisomers) or as mixtures of such. Further, when n is 1, the compounds of the invention are sulphoxides, which can exists in two enantiomeric forms, and the adjacent carbon can also exists in two enantiomeric forms. Compounds of general formula (1) can therefore exist as racemates, diastereoisomers, or single enantiomers, and the invention includes all possible isomers or isomer mixtures in all proportions. It is to be expected that for any given compound, one isomer may be more fungicidally active than another.

In a preferred group of the formula (1), $R^3$ and $R^4$ are independently H, $C_{1-3}$ alkyl, $C_{2-3}$ alkenyl or $C_{2-3}$ alkynyl provided that when both are other than H their combined total of carbon atoms does not exceed 4.

Preferably, in the compounds of formula (1), V is H, chloro, bromo or methyl.

In a preferred group of compounds of the formula (1) V is H.

In another preferred group of compounds of the formula (1) V is chloro.

In another preferred group of compounds of the formula (1) V is bromo.

In another preferred group of compounds of the formula (1) V is methyl.

Preferably, $R^3$ and $R^4$ are independently H or $C_{1-3}$ alkyl or $R^3$ and $R^4$ join with the carbon atom to which they are attached to form a 4 or 5-membered carbocyclic ring.

More preferably, $R^3$ and $R^4$ are independently H or $C_{1-3}$ alkyl.

It is particularly preferred, when $R^3$ and $R^4$ are both methyl.

More preferably, $R^3$ and $R^4$ join with the carbon atom to which they are attached to form a 4 or 5-membered carbocyclic ring.

Preferably, $R^5$ is H, $C_{1-4}$ alkyl, $C_{3-6}$ cycloalkyl, $C_{1-6}$ alkoxy-$C_{1-4}$ alkyl, $C_{3-6}$ alkenyloxy-$C_{1-4}$ alkyl, $C_{3-6}$ alkynyloxy-$C_{1-4}$ alkyl, $C_{1-4}$ hydroxyalkyl, or $C_{1-4}$ haloalkyl.

In a preferred group of compounds of the formula (1) $R^5$ is H.

In another preferred group of compounds of the formula (1) $R^5$ is $C_{1-4}$ alkyl.

In another preferred group of compounds of the formula (1) $R^5$ is methyl.

In another preferred group of compounds of the formula (1) $R^5$ is ethyl.

In another preferred group of compounds of the formula (1) $R^5$ is $C_{1-3}$ alkoxy-$C_{1-3}$ alkyl.

In another preferred group of compounds of the formula (1) $R^5$ is $C_{3-4}$ alkenyloxy-$C_{1-3}$ alkyl.

In another preferred group of compounds of the formula (1) $R^5$ is $C_{3-4}$ alkynyloxy-$C_{1-3}$ alkyl.

In another preferred group of compounds of the formula (1) $R^5$ is $C_{1-3}$ hydroxyalkyl.

In another preferred group of compounds of the formula (1) $R^5$ is $C_{1-3}$ haloalkyl.

In another preferred group of compounds of the formula (1) $R^5$ is $CH_2OH$, $CH_2OMe$, $CH_2OEt$, $CH_2OCH_2CHCH_2$, $CH_2OCH_2CCH$, $(CH_2)_2OMe$.

In a preferred group of compounds of the formula (1) V is H, chloro, bromo or methyl, $R^1$ is methyl, n is 0, $R^3$ and $R^4$ are independently $C_{1-3}$ alkyl and $R^5$ is H, $C_{1-4}$ alkyl or $C_{1-4}$ alkyl substituted with hydroxy, $C_{1-6}$ alkoxy, $C_{3-4}$ alkenyloxy or $C_{3-4}$ alkynyloxy.

Preferably, V is H, chloro, bromo or methyl, $R^1$ is methyl, n is 0, $R^3$ and $R^4$ are methyl and $R^5$ is H, $C_{1-4}$ alkyl optionally substituted with hydroxy, $C_{1-4}$ alkoxy, $C_{3-4}$ alkenyloxy or $C_{3-4}$ alkynyloxy.

Preferably, V is H, $R^1$ is methyl, n is 0, $R^3$ and $R^4$ are methyl and $R^5$ is H, $C_{1-4}$ alkyl optionally substituted with hydroxy, $C_{1-4}$ alkoxy, $C_{3-4}$ alkenyloxy or $C_{3-4}$ alkynyloxy.

Preferably, V is chloro, $R^1$ is methyl, n is 0, $R^3$ and $R^4$ are methyl and $R^5$ is H, $C_{1-4}$ alkyl optionally substituted with hydroxy, $C_{1-4}$ alkoxy, $C_{3-4}$ alkenyloxy or $C_{3-4}$ alkynyloxy.

Preferably, V is bromo, $R^1$ is methyl, n is 0, $R^3$ and $R^4$ are methyl and $R^5$ is H, $C_{1-4}$ alkyl optionally substituted with hydroxy, $C_{1-4}$ alkoxy, $C_{3-4}$ alkenyloxy or $C_{3-4}$ alkynyloxy.

Preferably, V is methyl, $R^1$ is methyl, n is 0, $R^3$ and $R^4$ are methyl and $R^5$ is H, $C_{1-4}$ alkyl optionally substituted with hydroxy, $C_{1-4}$ alkoxy, $C_{3-4}$ alkenyloxy or $C_{1-4}$ alkynyloxy.

Preferably, V is H, chloro, bromo or methyl, $R^1$ is methyl, n is 0, $R^3$ and $R^4$ are methyl and $R^5$ is $CH_2OH$, $CH_2OMe$, $CH_2OEt$, $CH_2OCH_2CHCH_2$, $CH_2OCH_2CCH$, $(CH_2)_2OMe$.

Compounds that form part of the invention are illustrated in Tables 1 to 6 below. Characterising data is given in Table 7 after the Examples.

TABLE 1

The compounds in Table 1 are of the general formula (1) where Ar is a group of the formula (A), V is H, $R^1$ is methyl, n is 0, $R^3$ and $R^4$ are methyl and $R^5$ has the values given in the table.

| Compound No | $R_5$ |
|---|---|
| 1 | H |
| 2 | $CH_3$ |
| 3 | $C_2H_5$ |
| 4 | $n\text{-}C_3H_7$ |
| 5 | $i\text{-}C_3H_7$ |
| 6 | $n\text{-}C_4H_9$ |
| 7 | $sec\text{-}C_4H_9$ |
| 8 | $iso\text{-}C_4H_9$ |
| 9 | $tert\text{-}C_4H_9$ |
| 10 | cyclopropyl |
| 11 | cyclobutyl |
| 12 | cyclopentyl |
| 13 | $FCH_2$ |
| 14 | $F_2CH$ |
| 15 | $FCH_2CH_2$ |
| 16 | $F_2CHCH_2$ |
| 17 | $F\text{-}n\text{-}C_3H_6$ |
| 18 | $HOCH_2$ |
| 19 | $HOCH_2CH_2$ |
| 20 | $CH_3OCH_2$ |
| 21 | $CH_3OCH_2CH_2$ |
| 22 | $C_2H_5OCH_2$ |
| 23 | $C_2H_5OCH_2CH_2$ |
| 24 | $CH_3(CH_3O)CH$ |
| 25 | $n\text{-}C_3H_7OCH_2$ |
| 26 | $n\text{-}C_3H_7OCH_2CH_2$ |
| 27 | $t\text{-}C_4H_9OCH_2$ |
| 28 | $t\text{-}C_4H_9OCH_2CH_2$ |
| 29 | $NC\text{—}C_2H_4$ |
| 30 | $NC\text{-}n\text{-}C_3H_6$ |
| 31 | $NC\text{-}n\text{-}C_4H_8$ |
| 32 | $(CH_3)_2C(CN)CH_2$ |
| 33 | $Cl_2CHCH_2$ |
| 34 | $Cl_2CH$ |
| 35 | $allylOCH_2$ |
| 36 | $allylOCH_2CH_2$ |
| 37 | $allylOCH_2CH_2CH_2$ |
| 38 | $propargylOCH_2$ |
| 39 | $propargylOCH_2CH_2$ |
| 40 | $propargylOCH_2CH_2CH_2$ |
| 41 | $CH_3OCH_2CH_2OCH_2$ |
| 42 | $CH_3OCH_2CH_2OCH_2CH_2$ |
| 43 | $C_2H_5OCH_2CH_2OCH_2$ |
| 44 | $C_2H_5OCH_2CH_2OCH_2CH_2$ |
| 45 | $CH_3OCH_2OCH_2$ |
| 46 | $C_2H_5OCH_2OCH_2$ |
| 47 | $tert\text{-}C_4H_9(CH_3)_2SiOCH_2$ |
| 48 | $tert\text{-}C_4H_9(CH_3)_2SiOC_2H_4$ |
| 49 | $ClCH_2$ |
| 50 | $ClCH_2CH_2$ |
| 51 | $Cl\text{-}n\text{-}C_3H_6$ |
| 52 | $BrCH_2$ |
| 53 | $BrCH_2CH_2$ |

TABLE 1-continued

The compounds in Table 1 are of the general formula (1) where Ar is a group of the formula (A), V is H, $R^1$ is methyl, n is 0, $R^3$ and $R^4$ are methyl and $R^5$ has the values given in the table.

| Compound No | $R_5$ |
|---|---|
| 54 | $Br\text{-}n\text{-}C_3H_6$ |
| 55 | $CH_3OCH_2CH_2OCH_2OCH_2$ |
| 56 | tetrahydropyran-2-yl$OCH_2$ |
| 57 | tetrahydrofuran-2-yl$OCH_2$ |
| 58 | Tetrahydrofuran-2-yl$CH_2$ |
| 59 | Oxiran-2-yl |
| 60 | Oxetan-2-yl |

Table 2 consists of compounds of the general formula (1) where Ar is a group of the formula (A), V is methyl, $R^1$ is methyl, n is 0, $R^3$ and $R^4$ are methyl and $R^5$ has the values given in the table 1.

Table 3 consists of compounds of the general formula (1) where Ar is a group of the formula (A), V is fluoro, $R^1$ is methyl, n is 0, $R^3$ and $R^4$ are methyl and $R^5$ has the values given in the table 1.

Table 4 consists of compounds of the general formula (1) where Ar is a group of the formula (A), V is chloro, $R^1$ is methyl, n is 0, $R^3$ and $R^4$ are methyl and $R^5$ has the values to given in the table 1.

Table 5 consists of compounds of the general formula (1) where Ar is a group of the formula (A), V is bromo, $R^1$ is methyl, n is 0, $R^3$ and $R^4$ are methyl and $R^5$ has the values given in the table 1.

Table 6 consists of compounds of the general formula (1) where Ar is a group of the formula (A), V is iodo, $R^1$ is methyl, n is 0, $R^3$ and $R^4$ are methyl and $R^5$ has the values given in the table 1.

The compounds of general formula (1) may be prepared as outlined in Schemes 1 to 4 below, in which Ar, $R^1$, $R^3$, $R^4$ and $R^5$ have the meanings given above, and $R^6$, see Scheme 1 below, is H or $C_{1-4}$ alkyl, as indicated; DMF is N,N-dimethylformamide, NBS is N-bromosuccinimide, NCS is N-chlorosuccinimide and MCPBA is m-chloroperbenzoic acid. Other abbreviations are defined in the text.

Compounds of formula (1), where n is 0, may be prepared as shown in Scheme 1. Esters of formula (2), where $R^6$ is $C_{1-4}$ alkyl, may be halogengenated to give halogenesters of formula (3), where Hal is a halogen atom such as bromine, chlorine or iodine, by reaction with a halogengenating agent such as N-bromosuccinimide, in a suitable solvent such as carbon tetrachloride or acetonitrile, in the presence of a radical initiator such as AIBN (azo-isobutyronitrile), and a light source, at between ambient temperature and the reflux temperature of the solvent. Compounds of general formula (3) are then reacted with alkanethiols of general formula $R^1SH$, in the presence of a base such as sodium hydride, in a suitable solvent such as DMF, to give compounds of general formula (6), or are reacted with alkanethiol salts $R^1S^-M^+$, where M is a metal such as sodium or lithium, in a suitable solvent such as DMF, to give compounds of general formula (6).

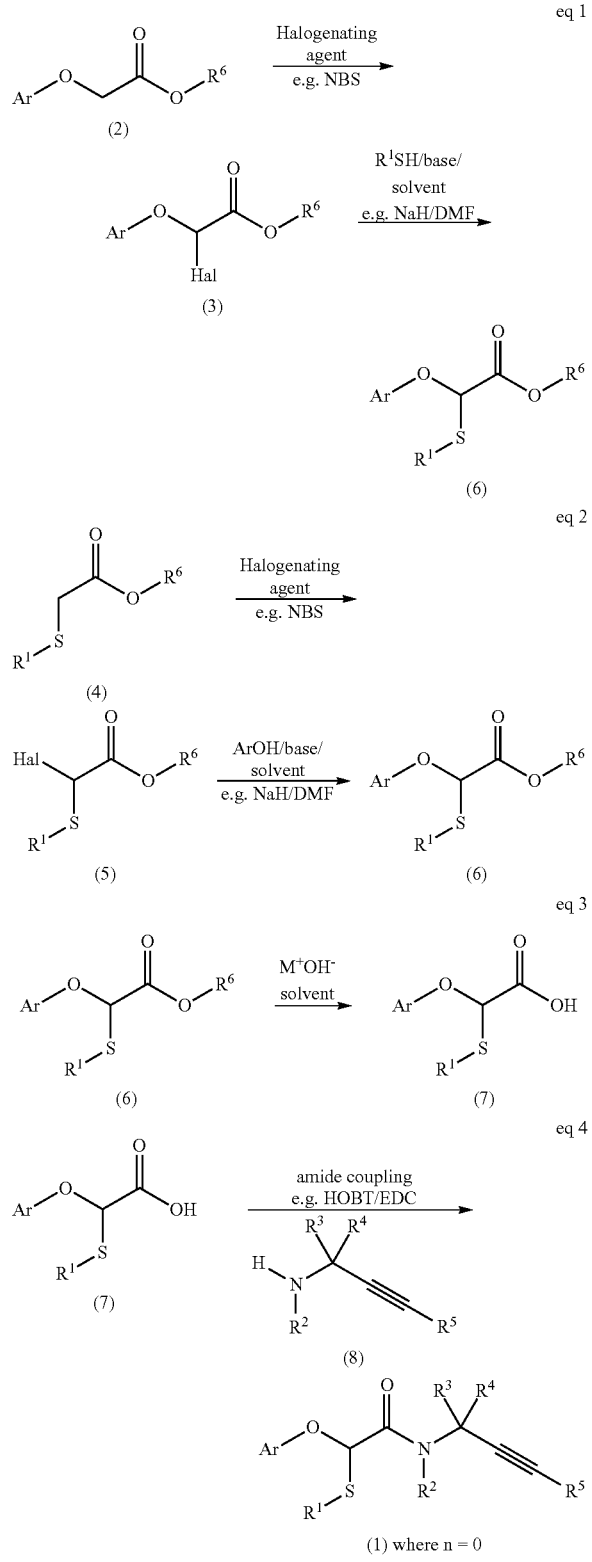

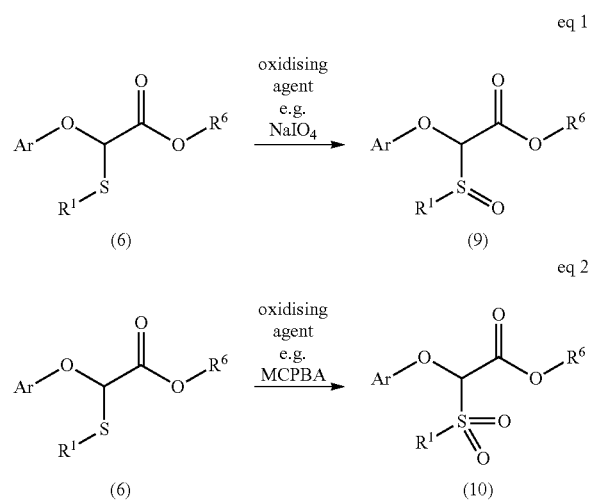

Alternatively esters of general formula (4) are halogenated to give halogenesters of formula (5), where Hal is a halogen atom such as bromine, chlorine or iodine, by reaction with a halogengenating agent such as N-chlorosuccinimide or N-bromosuccinimide, in a suitable solvent such as carbon tetrachloride or acetonitrile, at between 0° C. and the reflux temperature of the solvent. Halogenesters of formula (5) are reacted with hydroxy(hetero)-aryls ArOH, where Ar is as defined above, in the presence of a base such as potassium t-butoxide, potassium carbonate, or sodium hydride in a suitable solvent such as t-butanol, 1,4-dioxane or DMF, at between ambient temperature and the reflux temperature of the solvent, to give compounds of formula (6). Compounds of formula (6) are hydrolysed to acids of formula (7) by reaction with an alkali metal hydroxide $M^+OH^-$, in a suitable solvent such as aqueous methanol, ethanol, or THF (tetrahydrofuran) at between ambient temperature and the reflux temperature of the solvent. Acids of formula (7) can be condensed with amines of formula (8), wherein $R^2$ is hydrogen, using suitable activating agents such as HOBT (1-hydroxybenzotriazole) and EDC (1-ethyl-3-N,N-dimethylaminopropylcarbodiimide hydrochloride), at between 0° C. and ambient temperature, to give compounds of general formula (1) where n is 0.

Compounds of general formula (1), where n is 1 or 2, are prepared by oxidation to the sulphoxide (n is 1) or sulphone (n is 2) oxidation state, as shown in Scheme 2. For example, esters of the general formula (6) can be oxidised to sulphoxides of formula (9) with an oxidising agent such as sodium periodate in a suitable solvent such ethanol, between 0° C. and ambient temperature. Sulphones of formula (10) can be made either directly from compounds of formula (6) with two or more equivalents of an oxidising agent such as m-chloroperbenzoic acid (MCPBA), in a suitable solvent such as dichloromethane between 0° C. and the reflux temperature of the solvent, or from sulphoxides of formula (9) with one or more equivalents of m-chloroperbenzoic acid. Sulphides of formula (6), sulphoxides of formula (9) or sulphones of formula (10) can be hydrolysed to the corresponding acids (7), (11) or (12) by reaction with an alkali metal hydroxide in a suitable solvent such as ethanol at between 0° C. and the reflux temperature of the solvent followed by acidification. The acids of formula (7), (11) or (12) can be condensed with amines of formula (8), wherein $R^2$ is hydrogen, using suitable activating agents such as HOBT and EDC, at between 0° C. and ambient temperature, to give compounds of general formula (1) where n is 0, 1 or 2.

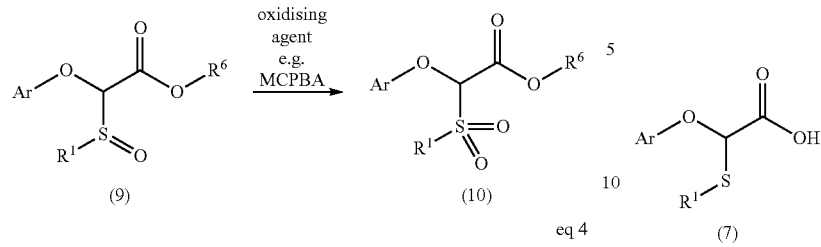
eq 3
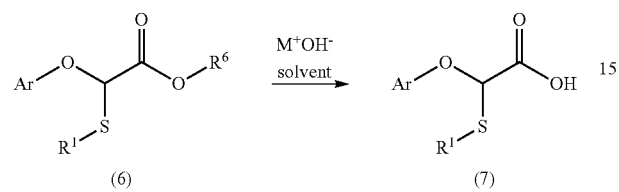
eq 4
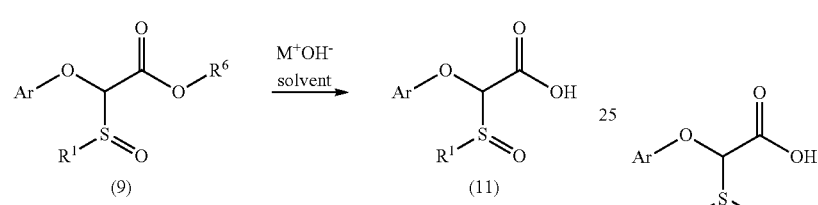
eq 5
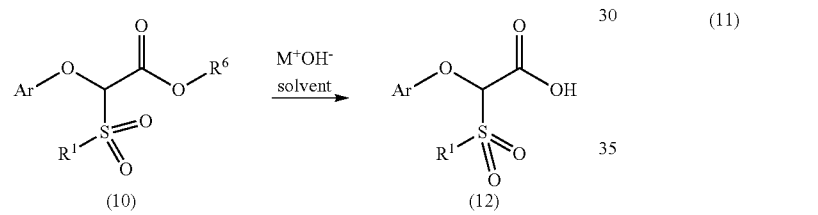
eq 6
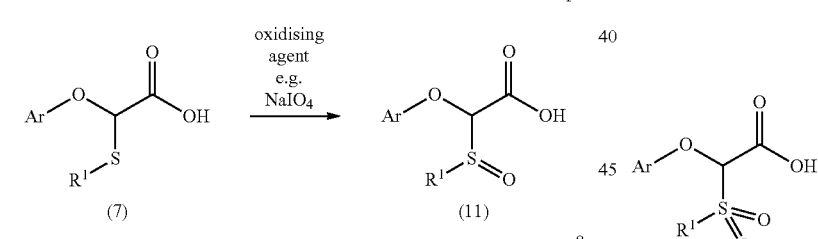
eq 7
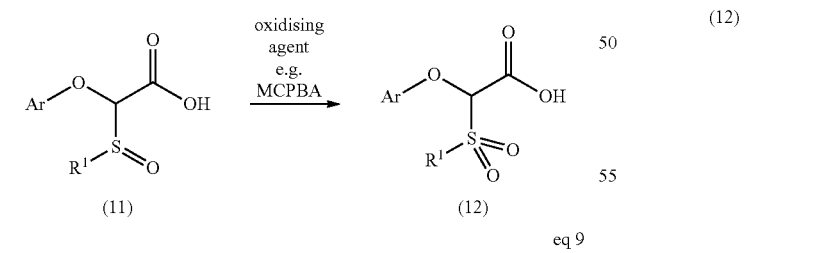
eq 8
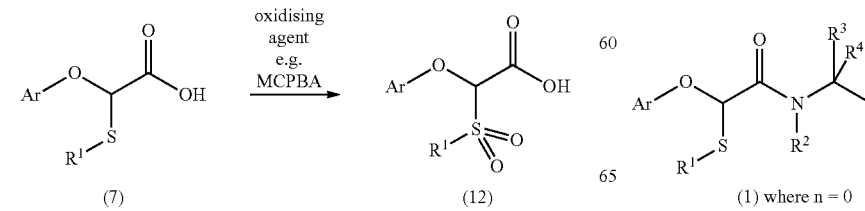
eq 9
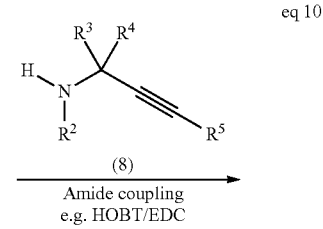
eq 10
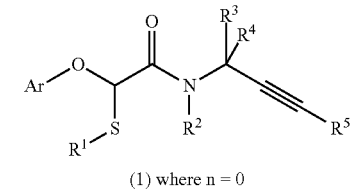
eq 11
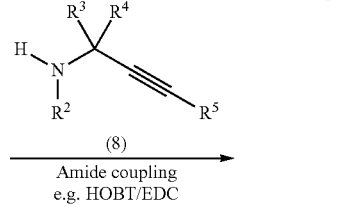
eq 12
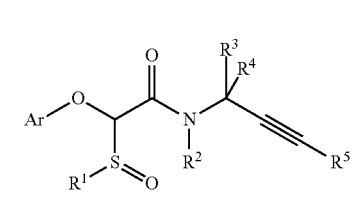
eq 13

-continued

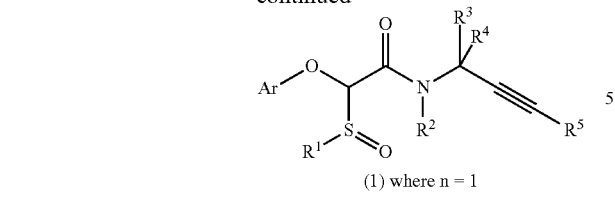

(1) where n = 1 eq 14 ↓ oxidising agent e.g. MCPBA

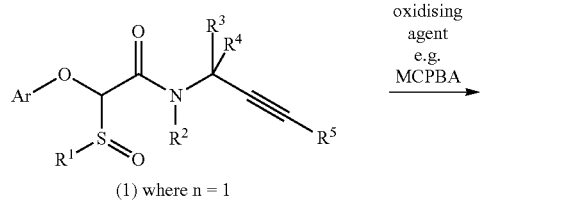

(1) where n = 1

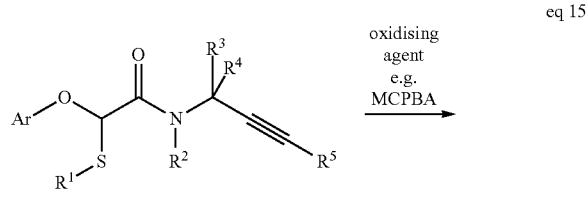

(1) where n = 2

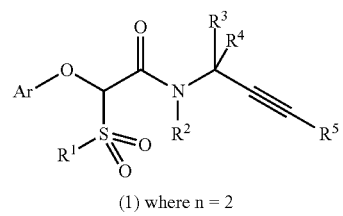

(1) where n = 0 eq 15 ↓ oxidising agent e.g. MCPBA

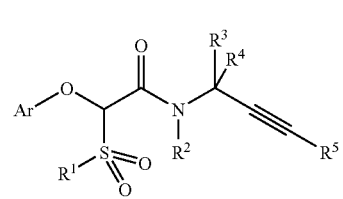

(1) where n = 2

Similarly, sulphoxides of formula (11) and of formula (1) where n is 1 can be prepared from sulphides of formula (7) and of formula (1) where n is 0 respectively, using oxidising agents such as sodium metaperiodate or m-chloroperbenzoic acid as described above. Sulphones of formula (12) and of formula (1) where n is 2, can be prepared either from sulphides of formula (7) and of formula (1) where n is 0, by using at least two equivalents of oxidising agents such as m-chloroperbenzoic acid, or from sulphoxides of formula (11) and of formula (1) where n is 1, using one or more equivalents of oxidising agents such as m-chloroperbenzoic acid, as described above.

Compounds of formula (1) can also be prepared as shown in Scheme 3. Acids of formula (13) can be condensed with amines of formula (8), wherein $R^2$ is hydrogen, using suitable activating agents such as HOBT and EDC, at between 0° C. and ambient temperature, to give compounds of formula (14). Compounds of formula (14) can be halogengenated to compounds of formula (16) using a halogengenating agent such as N-chlorosuccinimide, in a suitable solvent such as carbon tetrachloride or acetonitrile, at between 0° C. and ambient temperature. Amides of formula (16) can also be prepared from acid halides of formula (15) by reaction with amines of formula (8), wherein $R^2$ is hydrogen, in the presence of a base such as triethylamine in a suitable solvent such as dichloromethane, at between 0° C. and ambient temperature.

Scheme 3 eq 1

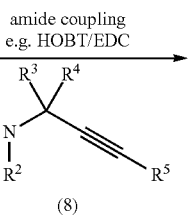

(13)

amide coupling e.g. HOBT/EDC

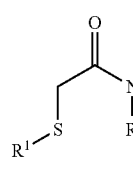

(8)

↓

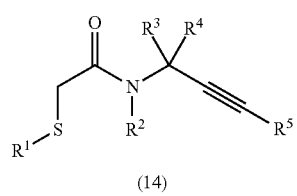

(14)

eq 2

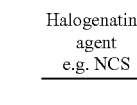

(14)

Halogenating agent e.g. NCS →

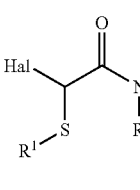

(16)

eq 3

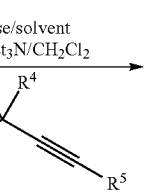

(15)

base/solvent e.g. Et$_3$N/CH$_2$Cl$_2$

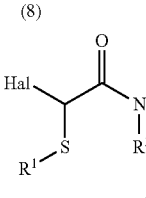

(8)

↓

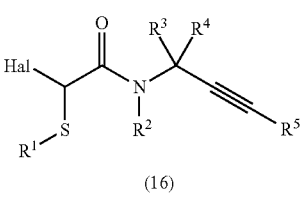

(16)

eq 4

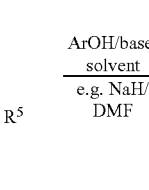

(16)

ArOH/base/ solvent e.g. NaH/ DMF →

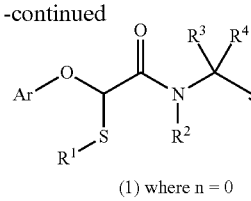

(1) where n = 0

Halogensulphides of formula (16) can be reacted with hydroxy(hetero)aryls ArOH, in the presence of a base such as potassium carbonate or sodium hydride, in a suitable solvent such as DMF, at between 0° C. and 80° C., to give compounds of formula (1) where n is 0.

As shown in Scheme 4, amines of the general formula (20), which are examples of amines of the general formula (8) wherein $R^2$ is H, may be prepared by alkylation of a silyl-protected aminoalkyne of the general formula (18) using a suitable base, such as n-butyl lithium, followed by reaction with a suitable alkylating reagent $R^5LG$, such as an alkyl iodide, for example, methyl iodide, to form an alkylated compound of the general formula (19). In a similar procedure, a silyl-protected aminoalkyne of the general formula (18) may be reacted with a carbonyl derivative $R^aCOR^b$, for example formaldehyde, using a suitable base, such as n-butyl lithium, to provide an aminoalkyne (19) containing a hydroxyalkyl moiety. The silyl protecting group may then be removed from a compound of the general formula (19) with, for example, an aqueous acid to form an aminoalkyne of the general formula (20). Aminoalkynes of the general formula (20) may be further derivatised, for instance when $R^5$ is a hydroxyalkyl group, for example, by reacting a compound of the general formula (20) with a silylating agent, for example t-butyldimethylsilyl chloride, to give a derivative silylated on oxygen of the general formula (21). In addition, a compound of the general formula (20) may be treated with a base, such as sodium hydride or potassium bis(trimethylsilyl)amide followed by a compound $R^cLG$, to give a compound of the general formula (22). In an alternative sequence, a compound of general formula (19) may be treated with a base, such as sodium or potassium bis(trimethylsilyl)amide, followed by a compound $R^cLG$, where LG represents a leaving group such as a halogengen, or sulphonate ester such as $OSCO_2Me$, or $OSO_2$-4-tolyl, for example ethyl iodide, to give, after removal of the silyl protecting group, compounds of general formula (22).

Scheme 4

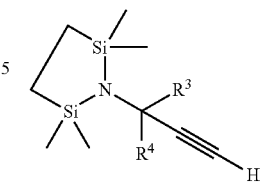

(18)

eq 2
1. base
2. $R^5LG$
or $R^aCOR^b$

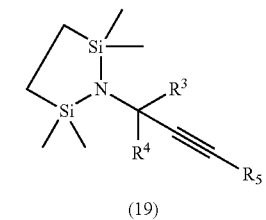

(19)

eq 3

$H_3O^+$

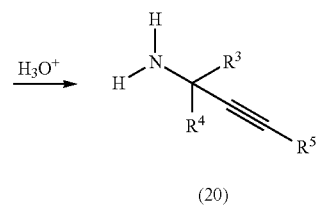

(19)

(20)

eq 4 e.g. $R^5 = CH_2OH$
$R^cLG$

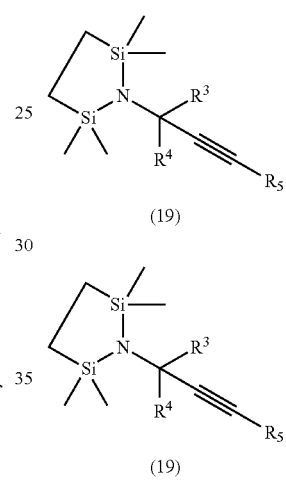

(19)

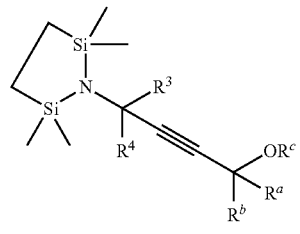

(23)

eq 5 base
$R^cLG$ e.g. $R^5 = CH_2OH$

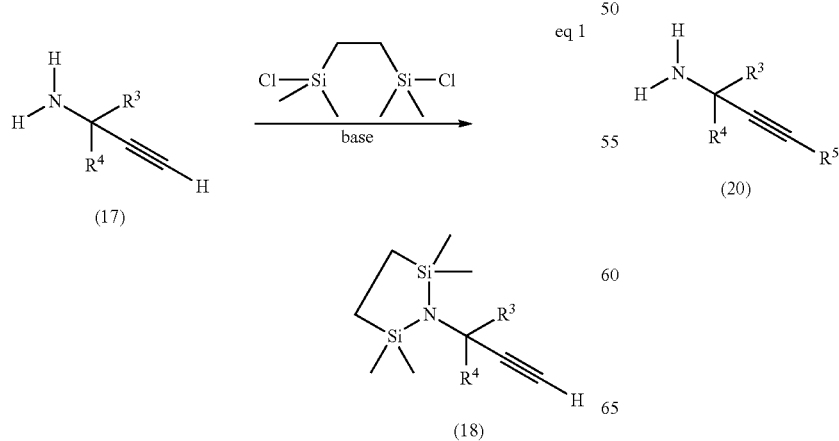

(17)

(18)

(20)

(22)

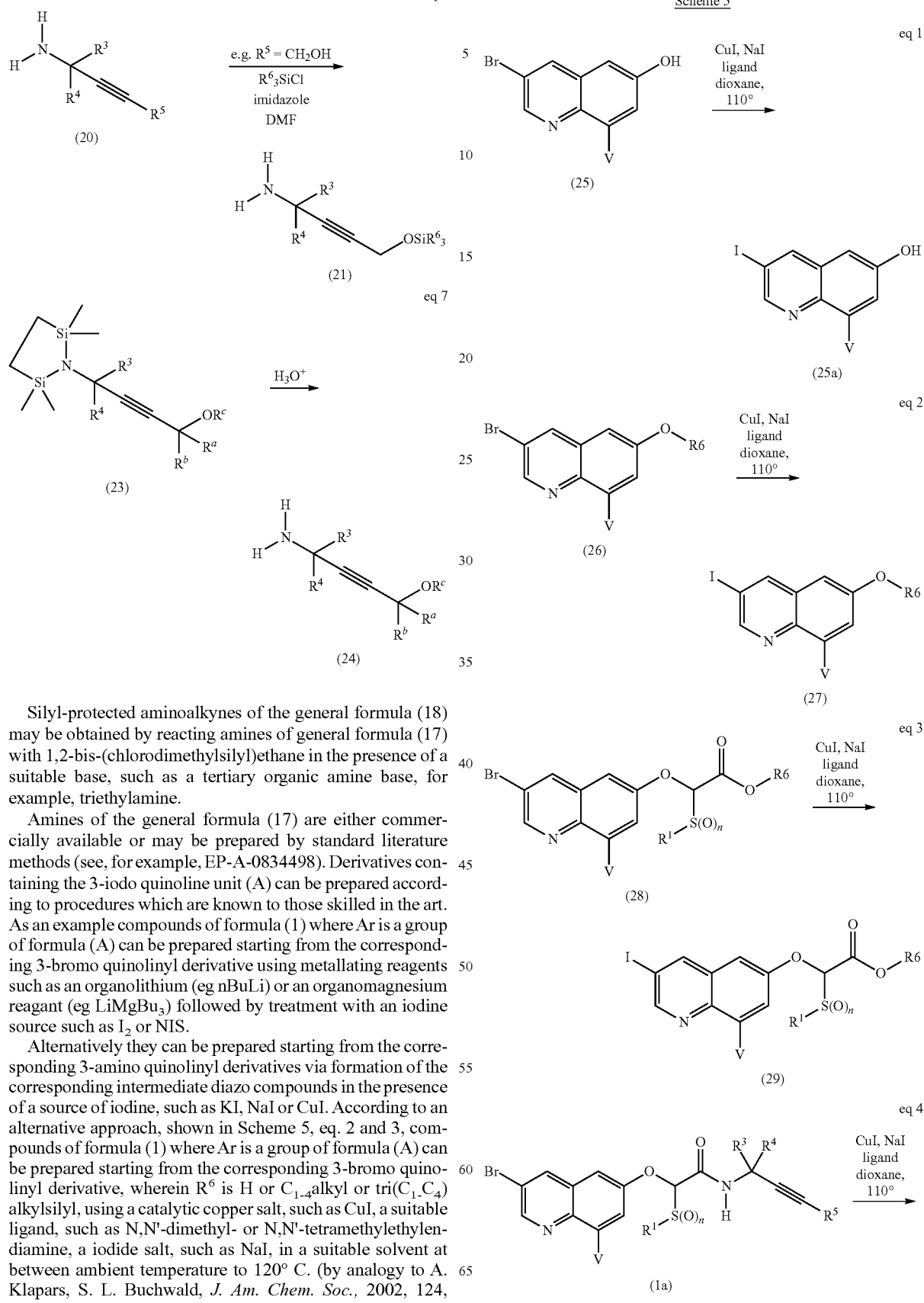

Silyl-protected aminoalkynes of the general formula (18) may be obtained by reacting amines of general formula (17) with 1,2-bis-(chlorodimethylsilyl)ethane in the presence of a suitable base, such as a tertiary organic amine base, for example, triethylamine.

Amines of the general formula (17) are either commercially available or may be prepared by standard literature methods (see, for example, EP-A-0834498). Derivatives containing the 3-iodo quinoline unit (A) can be prepared according to procedures which are known to those skilled in the art. As an example compounds of formula (1) where Ar is a group of formula (A) can be prepared starting from the corresponding 3-bromo quinolinyl derivative using metallating reagents such as an organolithium (eg nBuLi) or an organomagnesium reagant (eg LiMgBu$_3$) followed by treatment with an iodine source such as I$_2$ or NIS.

Alternatively they can be prepared starting from the corresponding 3-amino quinolinyl derivatives via formation of the corresponding intermediate diazo compounds in the presence of a source of iodine, such as KI, NaI or CuI. According to an alternative approach, shown in Scheme 5, eq. 2 and 3, compounds of formula (1) where Ar is a group of formula (A) can be prepared starting from the corresponding 3-bromo quinolinyl derivative, wherein R$^6$ is H or C$_{1-4}$alkyl or tri(C$_1$-C$_4$) alkylsilyl, using a catalytic copper salt, such as CuI, a suitable ligand, such as N,N'-dimethyl- or N,N'-tetramethylethylendiamine, a iodide salt, such as NaI, in a suitable solvent at between ambient temperature to 120° C. (by analogy to A. Klapars, S. L. Buchwald, *J. Am. Chem. Soc.*, 2002, 124, 14844-14845).

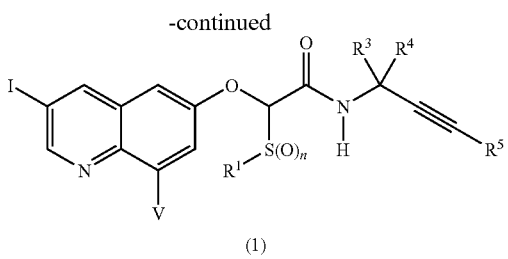

(1)

The compounds of the formulae (25a) and (27) are novel and have been specifically designed as intermediates for the synthesis of the compounds of the formula (1).

The compounds of formula (1) are active fungicides and may be used to control one or more of the following pathogens: *Pyricularia oryzae* (*Magnaporthe grisea*) on rice and wheat and other *Pyricularia* spp. on other hosts; *Puccinia triticina* (or *recondita*), *Puccinia striiformis* and other rusts on wheat, *Puccinia hordei*, *Puccinia striiformis* and other rusts on barley, and rusts on other hosts (for example turf, rye, coffee, pears, apples, peanuts, sugar beet, vegetables and ornamental plants); *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Levelhila taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerefia cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; other downy mildews, such as *Bremia lactucae* on lettuce, *Peronospora* spp. on soybeans, tobacco, onions and other hosts, *Pseudoperonospora humuli* on hops and *Pseudoperonospora cubensis* on cucurbits; *Pythium* spp. (including *Pythium ultimum*) on turf and other hosts; *Phytophthora infestans* on potatoes and tomatoes and other *Phytophthora* spp. on vegetables, strawberries, avocado, pepper, ornamentals, tobacco, cocoa and other hosts; *Thanatephorus cucumeris* on rice and turf and other *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp., *Typhula* spp., *Microdochium nivale*, *Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; post-harvest diseases particularly of fruit (for example *Penicillium digitatum*, *Penicillium italicum* and *Trichoderma viride* on oranges, *Colletotrichum musae* and *Gloeosporium musarum* on bananas and *Botrytis cinerea* on grapes); other pathogens on vines, notably *Eutypa lata*, *Guignardia bidwellii*, *Phellinus igniarus*, *Phomopsis viticola*, *Pseudopeziza tracheiphila* and *Stereum hirsutum*; other pathogens on trees (for example *Lophodermium seditiosum*) or lumber, notably *Cephalogenascus fragrans*, *Ceratocystis* spp., *Ophiostoma piceae*, *Penicillium* spp., *Trichoderma pseudokoningii*, *Trichoderma viride*, *Trichoderma harzianum*, *Aspergillus niger*, *Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

The compounds of formula (1) show particularly good activity against the Oomycete class of pathogens such as *Phytophthora infestans*, *Plasmopara* species, e.g. *Plasmopara viticola* and *Pythium* species e.g. *Pythium ultimum*.

A compound of formula (1) may move acropetally, basipetally or locally in plant tissue to be active against one or more fungi. Moreover, a compound of formula (1) may be volatile enough to be active in the vapour phase against one or more fungi on the plant.

The invention therefore provides a method of combating or controlling phytopathogenic fungi which comprises applying a fungicidally effective amount of a compound of formula (1), or a composition containing a compound of formula (1), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (1) are preferably used for agricultural, horticultural and turfgrass purposes in the form of a composition.

In order to apply a compound of formula (1) to a plant, to a seed of a plant, to the locus of the plant or seed or to soil or any other growth medium, a compound of formula (1) is usually formulated into a composition which includes, in addition to the compound of formula (1), a suitable inert diluent or carrier and, optionally, a surface active agent (SFA). SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (1). The composition is generally used for the control of fungi such that a compound of formula (1) is applied at a rate of from 0.1 g to 10 kg per hectare, preferably from 1 g to 6 kg per hectare, more preferably from 1 g to 1 kg per hectare.

When used in a seed dressing, a compound of formula (1) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (1) and a suitable carrier or diluent therefor.

In a still further aspect the invention provides a method of combating and controlling fungi at a locus, which comprises treating the fungi, or the locus of the fungi with a fungicidally effective amount of a composition comprising a compound of formula (1).

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (1).

Dustable powders (DP) may be prepared by mixing a compound of formula (1) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (1) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (1) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (1) and one or more powdered solid diluents or carriers, or from pre-formed blank granules by absorbing a compound of formula (1) (or a solution thereof, in a suitable agent) in a porous granular material (such as pumice, attapulgite clays, fuller's earth, kieselguhr, diatomaceous earths or ground corn cobs) or by adsorbing a compound of formula (1) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (1) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (1) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octyl-pyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of formula (1) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SFAs, to produce spontaneously a thermodynamically stable isotropic liquid formulation. A compound of formula (1) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (1). SCs may be prepared by ball or bead milling the solid compound of formula (1) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (1) may be dry milled and added to water, containing agents hereinbefore described, to produce the desired end product.

Aerosol formulations comprise a compound of formula (1) and a suitable propellant (for example n-butane). A compound of formula (1) may also be dissolved or dispersed in a suitable medium (for example water or a water miscible liquid, such as n-propanol) to provide compositions for use in non-pressurised, hand-actuated spray pumps.

A compound of formula (1) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (1) and, optionally, a carrier or diluent therefor. The polymeric shell may be produced by either an interfacial polycondensation reaction or by a coacervation procedure. The compositions may provide for controlled release of the compound of formula (1) and they may be used for seed treatment. A compound of formula (1) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (1)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (1)).

A compound of formula (1) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (1) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (1) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (1) (for example 0.0001 to 10%, by weight) depending upon the purpose for which they are to be used.

A compound of formula (1) may be used in mixtures with fertilisers (for example nitrogen-, potassium- or phosphorus-containing fertilisers). Suitable formulation types include granules of fertiliser. The mixtures suitably contain up to 25% by weight of the compound of formula (1).

The invention therefore also provides a fertiliser composition comprising a fertiliser and a compound of formula (1).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (1) alone. Further the other fungicide may have a synergistic effect on the fungicidal activity of the compound of formula (1).

The compound of formula (1) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (1); or help to overcome or prevent the development of resistance to individual components. The particular additional active ingredient will depend upon the intended utility of the composition.

Examples of fungicidal compounds which may be included in the composition of the invention are AC 382042 (N-(1-cyano-1,2-dimethylpropyl)-2-(2,4-dichlorophenoxy) pro-pionamide), acibenzolar-S-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone, CGA 41396, CGA 41397, chinomethionate, chlorbenzthiazone, chlorothalogennil, chlorozolinate, clozylacon, copper containing compounds such as copper oxychloride, copper oxyquinolate, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, O,O-di-iso-propyl-S-benzyl thiophosphate, dimefluazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)-N-benzyl-N([methyl(methyl-thioethylideneaminooxy-carbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazole, sipconazole, sodium pentachlorophenate, spiroxamine, streptomycin, sulphur, tebuconazole, tecloftalam, tecnazene, tetraconazole, thiabendazole, thifluzamide, 2-(thiocyano-methylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and compounds of the formulae:

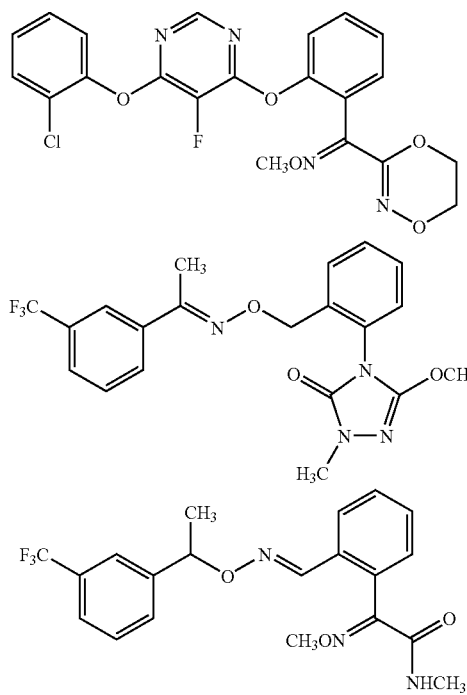

The compounds of formula (1) may be mixed with soil, peat or other rooting media for the protection of plants against seed-borne, soil-borne or foliar fungal diseases.

Some mixtures may comprise active ingredients, which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples.

EXAMPLE 1

This Example illustrates the preparation of 2-(3-iodoquinolinyl-6-oxy)-2-methylthio-N-(2-methylbut-3-yn-2-yl) acetamide (Compound No 1 of Table 1, No 1 of Table 7) as shown in Scheme 1.

Step 1: To a Stirred Solution of ethyl (methylthio)acetate (10.8 ml) in dichloromethane (300 ml) cooled to −15° C. is added dropwise sulphuryl chloride (8.1 ml). The mixture is allowed to warm to room temperature over two hours and then concentrated under reduced pressure to give crude chloromethylsulfanyl-acetic acid ethyl ester as a colourless liquid.

The product is used in the next step without further purification. ¹H NMR (CDCl₃) δ ppm: 5.35 (1H, s); 4.25 (2H, m); 2.30 (3H, s); 1.30 (3H, t).

Step 2: Preparation of 3-iodo-6-hydroxyquinoline

To a stirred mixture of 3-bromo-6-hydroxyquinoline (preparation described in Liebigs Ann Chem 1966, 98-106), (3.0 g), sodium iodide (4.0 g) and copper iodide (0.25 g) in dioxane (19.5 ml) is added N,N'-tetramethyl-ethane-1,2-diamine (0.24 g) in a sealed tube under argon. The mixture is stirred at 120° C. for 14 h and upon cooling is treated with aqueous ammonia followed by aqueous hydrochloric acid to reach pH 5. Extraction with ethyl acetate, drying of the organic phase over magnesium sulphate, filtration and evaporation under reduced pressure gives the required product ((M+1)⁺272) as a light brown coloured powder that is used as such in the next step.

Step 3: Preparation of ethyl 2-(3-iodoquinolinyl-6-oxy)-2-methylthio acetate

3-Iodo-quinolin-6-ol (1.0 g) from Step 2 is dissolved in dry DMF (10 ml). 2-chloro-2-methylsulfanyl-acetic acid ethyl ester (740 mg) and dry potassium carbonate (1.4 g) are added to the mixture at R. T. The resulting suspension is stirred at 50° C. for 3 hour. The reaction mixture is poured into brine and extracted 3 times with ethyl acetate. The organic layers are combined, wahed with brine, dried over sodium sulphate, filtered and evaporated. After flash chromatography (cyclohexane: ethyl acetate, 2:1) 1.05 g of ethyl 2-(3-iodo-quinolin-6-yloxy)-2-methylthio acetate are obtained as a pale yellow solid. ¹H NMR (CDCl₃) δ ppm: 8.90 (1H, d); 8.45 (1H, d); 8.00 (1H, d); 7.50 (1H, dd); 7.10 (1H, d); 5.70 (1H, s); 4.35 (2H, m); 2.22 (3H, s); 1.35 (3H, t).

Step 4: Preparation of 2-(3-Iodoquinolinyl-6-oxy)-2-methylthio acetic acid

To a solution of ethyl 2-(3-iodoquinolinyl-6-oxy)-2-methylthio acetate (1.05 g) in tetrahydrofurane (20 ml) at 0° C. is added a 0.5 M aqueous solution of NaOH (6.8 ml). The reaction mixture is stirred 4 h at room temperature. Ethyl acetate is added and the two phases are separated. The aqueous phase is acidified with 1M HCl (until pH 2-3) then extracted twice with ethyl acetate. The organic phases are combined, ished with brine, dried over sodium sulphate, filtered and evaporated to give 0.90 g of crude 2-(3-iodoquinolinyl-6-oxy)-2-methylthio acetic acid which is used in the next step without further purification. ¹H NMR (DMSO-d₆) δ ppm: 13.5 (1h, br s); 8.90 (1H, d); 8.70 (1H, d); 7.95 (1H, d); 7.55 (1H, dd); 7.40 (1H, d); 6.05 (1H, s); 2.15 (3H, s).

Step 5: 2-(3-iodoquinolinyl-6-oxy)-2-methylthio-N-(2-methylbut-3-yn-2-yl) acetamide 2-(3-Iodo-quinolinyl-6-oxy)-2-methylthio acetic acid (250 mg), N-(2-methylbut-3-yn-2-yl) amine (67 mg), 1-hydroxy-7-azabenzotriazole (HOAT) (109 mg), O-(Benzotriazol-1-yl)-N,N,N',N'-tetramethyluronium tetrafluoroborate (TBTU) (257 mg) and triethylamine (0.3 ml) in dry CH₃CN (8 ml) are stirred at ambient temperature overnight. The reaction mixture is quenched with a saturated solution of NaHCO₃ and extracted with ethyl acetate. The organic phase is washed with brine and dried over sodium sulphate, filtered and evaporated. The crude product is purified by flash chromatography (cyclohexane: ethyl acetate, 3:1) to give 233 mg of 2-(3-iodoquinolinyl-6-oxy)-2-methylthio-N-(2-methylbut-3-yn-2-yl) acetamide as a white solid.

Compound 1 of Table 1: ¹H NMR (CDCl₃) δ ppm: 8.95 (1H, d); 8.45 (1H, d); 8.05 (1H, d); 7.45 (1H, dd); 7.15 (1H, d); 6.70 (1H, br s); 5.62 (1H, s); 2.40 (1H, s); 2.20 (3H, s); 1.72 (6H, s).

The following amides are prepared using a similar procedure.

2-(3-iodoquinolinyl-6-oxy)-2-methylthio-N-(2-methylpent-3-yn-2-yl) acetamide (Compound No 2 of Table 1 and No 2 of Table 7), 2-(3-iodoquinolinyl-6-oxy)-2-methylthio-N-(2-methylhex-3-yn-2-yl) acetamide (Compound No 3 of Table 1 and No 5 of Table 7), 2-(3-iodoquinolinyl-6-oxy)-2-methylthio-N-(5-methoxy-2-methylpent-3-yn-2-yl) acetamide (Compound No 20 of Table 1 and No 3 of Table7), 2-(3-iodoquinolinyl-6-oxy)-2-methylthio-N-(6-methoxy-2-methylhex-3-yn-2-yl) acetamide (Compound No 21 of Table 1 and No 4 of Table 7), 2-(3-iodoquinolinyl-6-oxy)-2-methylthio-N-(2-ethylbut-3-yn-2-yl) acetamide (Compound No 6 of Table 7), 2-(3-iodoquinolinyl-6-oxy)-2-methylthio-N-(2-ethylpent-3-yn-2-yl) acetamide (Compound No 7 of Table 7).

EXAMPLE 2

This Example illustrates the preparation of 2-(3-iodo-8-methyl-quinolinyl-6-oxy)-2-methylthio-N-(2-methylpent-3-yn-2-yl) acetamide (Compound No 2 of Table 2 and No 9 of Table7).

Step 1: Preparation of 3-bromo-8-methyl-6-hydroxyquinoline

6-Amino-3-bromo-8-methylquinoline (12 g) (preparation described in Journal of the American Chemical Society (1955), pages 4175-4176) is suspended in a mixture of water (5 ml) and phosphoric acid (60 ml) and heated in a sealed glass tube to 180° C. for 3 days. The mixture is cooled to ambient temperature, diluted with water then taken to pH 3-4 with aqueous (2M)
sodium hydroxide. The precipitate formed is filtered from solution, washed with cold water and sucked to dryness to give 3-bromo-6-hydroxy-8-methylquinoline as a grey solid.

¹H NMR (d6-DMSO) δ ppm: 8.61 (1H, d); 8.38 (1h, d); 7.15 (1H, d); 6.91 (1H, d); 2.56 (3H, s).

The procedures of Example 1, steps 2-5 are repeated using 3-bromo-8-methyl-6-hydroxy-quinoline from step 1 of Example 2 above as a starting material to provide 2-(3-iodo-8-methyl-quinolin-6-yloxy)-N-(2-methylpent-3-yn-2-yl) acetamide as a pale yellow solid Compound 2 of Table 2: ¹H NMR (CDCl₃) δ ppm: 8.93 (1H, d); 8.41 (1H, d); 7.30 (1H, d); 6.97 (1H, d); 6.70 (1H, br s); 5.60 (1H, s); 2.75 (3H, s); 2.20 (3H, s); 1.82 (3H, s); 1.70 (3H, s); 1.68 (3H, s).

The following amides are prepared using a similar procedure.

2-(3-iodo-8-methyl-quinolinyl-6-oxy)-2-methylthio-N-(2-methylbut-3-yn-2-yl) acetamide (Compound No 1 of Table 2 and No 8 of Table 7), 2-(3-iodo-8-methyl-quinolinyl-6-oxy)-2-methylthio-N-(2-methylhex-3-yn-2-yl)acetamide (Compound No 3 of Table 2 and No 12 of Table 7), 2-(3-iodo-8-methyl-quinolinyl-6-oxy)-2-methylthio-N-(5-methoxy-2-methylpent-3-yn-2-yl) acetamide (Compound No 20 of Table 2 and No 10 of Table 7), 2-(3-iodo-8-methyl-quinolinyl-6-oxy)-2-methylthio-N-(6-methoxy-2-methylhex-3-yn-2-yl) acetamide (Compound No 21 of Table 2 and No 11 of Table 7), 2-(3-iodo-8-methyl-quinolinyl-6-oxy)-2-methylthio-N-(2-ethylbut-3-yn-2-yl) acetamide (Compound No 13 of Table 7), 2-(3-iodo-8-methyl-quinolinyl-6-oxy)-2-methylthio-N-(2-ethylpent-3-yn-2-yl) acetamide (Compound No 14 of Table 7).

EXAMPLE 3

This Example illustrates the preparation of 2-(8-chloro-3-iodo-quinolinyl-6-oxy)-2-methylthio-N-(2-methylbut-3-yn-2-yl) acetamide (Compound No 1 of Table 4 and No 15 of Table7).

Step 1: Preparation of 8-chloro-3-iodo-6-hydroxyquinoline

To a stirred mixture of 3-bromo-8-chloro-6-hydroxyquinoline (5.0 g) (preparation described in WO 2004/108663), sodium iodide (5.8 g) and copper iodide (0.37 g) in dioxane (65 ml) is added N,N"-dimethyl-ethane-1,2-diamine (0.34 g) in a sealed tube under argon. The mixture is stirred at 120° C. for 14 h and upon cooling is treated with aqueous ammonia followed by aqueous hydrochloric (to pH 5). Extraction with ethyl acetate, drying of the organic phase over magnesium sulphate, filtration and evaporation under reduced pressure gives the required product ((M+1)$^+$306) that is used as such in the next step.

The procedures of example 1, steps 3 to 5 are repeated using 8-chloro-3-iodo-6-hydroxyquinoline from Step 1 above as a starting material to provide 2-(8-chloro-3-iodo-quinolinyl-6-oxy)-2-methylthio-N-(2-methylbut-3-yn-2-yl) acetamide as a white solid (Compound No 1 of Table 4) $^1$H NMR (CDCl$_3$) δ ppm: 9.05 (1H, d); 8.50 (1H, d); 7.61 (1H, d); 7.10 (1H, d); 6.68 (1H, br s); 5.60 (1H, s); 2.40 (1H, s); 2.20 (3H, s); 1.72 (6H, s). (M+1)$^+$: 475.

The following amides are prepared using a similar procedure.

2-(8-chloro-3-iodo-quinolinyl-6-oxy)-2-methylthio-N-(2-methylpent-3-yn-2-yl) acetamide (Compound No 2 of Table 4 and No 16 of Table 7), 2-(8-chloro-3-iodo-quinolinyl-6-oxy)-2-methylthio-N-(5-methoxy-2-methylpent-3-yn-2-yl) acetamide (Compound No 20 of Table 2 and No 17 of Table 7).

EXAMPLE 4

This Example illustrates the preparation of 2-(8-bromo-3-iodo-quinolinyl-6-oxy)-2-methylthio-N-(2-methylbut-3-yn-2-yl)acetamide (Compound No 1 of Table 5 and No 18 of Table7).

Step 1: Preparation of 8-bromo-3-iodo-6-hydroxyquinoline

Stage 1: In a similar procedure to Step 2 of Example 1 8-amino-3-bromo-6-methoxyquinoline (preparation described in *Journal of Pharmaceutical Sciences* (1984), 73(12), 1854-6) (6.0 g) is treated with sodium iodide, copper iodide and N,N'-dimethyl-ethane-1,2-diamine in dioxane in a sealed tube under argon, at 120° C. for 14 h. After work-up the crude is purified by flash chromatography (ethyl acetate:cyclohexane, 1:4) to provide 8-amino-3-iodo-6-methoxyquinoline (4.6 g) as a pure product. $^1$H NMR (CDCl$_3$) δ ppm: 8.70 (1H, d); 8.30 (1H, d); 6.55 (1H, d); 6.35 (1H, d); 5.00 (2H, br s); 3.85 (3H, s). (M+1)$^+$: 301

Stage 2: A suspension of 8-amino-3-iodo-6-methoxyquinoline (2.0 g) in HBr (20 ml) cooled to 0° C. is treated with a solution of sodium nitrite (0.48 g) in water (4 ml). The thick cold suspension is then added portionwise to a purple solution of CuBr$_2$ (1.64 g) in 10 ml of conc. HBr preheated at 60° C. After 3 h an aqueous solution of NH$_4$OH is added to the mixture to reach pH 14. After filtration of the mixture the filtrate is purified by flash chromatography (CH$_2$Cl$_2$) providing 8-bromo-3-iodo-6-methoxyquinoline (2.2 g) as a pale yellow solid. $^1$H NMR (CDCl$_3$) δ ppm: 8.92 (1H, d); 8.32 (1H, d); 7.65 (1H, d); 6.82 (1H, d); 3.87 (3H, s).

Stage 3: A mixture of 8-bromo-3-iodo-6-methoxyquinoline (0.92 g) and conc HBr (11 ml) is heated at reflux during 3 days until no starting material can be detected. After addition of 2 M aq NaOH to reach pH 5 the mixture is extracted with ethyl acetate, the organic phase washed with brine and dried over anhydrous Na$_2$SO$_4$ Evaporation of the organic phase gives 8-bromo-3-iodo-6-hydroxyquinoline as a crude product which is used as such in the next step. $^1$H NMR (DMSO-d$_6$) δ ppm: 10.50 (1H, br s); 8.9 (1H, d); 8.73 (1H, d); 7.70 (1H, d); 7.15 (1H, d). (M+1)$^+$: 350/352.

The procedures of example 1, steps 3 to 5 are repeated using 8-bromo-3-iodo-6-hydroxyquinoline from Step 1, Stage 3 above as a starting material to provide 2-(8-bromo-3-iodo-quinolinyl-6-oxy)-2-methylthio-N-(2-methylpent-3-yn-2-yl) acetamide (Compound No 2 of Table 5 and No 19 of Table 7). $^1$H NMR (CDCl$_3$) δ ppm: 9.02 (1H, d); 8.48 (1H, d); 7.82 (1H, d); 7.12 (1H, d); 6.70 (1H, br s); 5.60 (1H, s); 2.20 (3H, s); 1.80 (3H, s); 1.70 (3H, s); 1.69 (3H, s). Mp: 161-162° C.; (M+1)$^+$: 533-535.

The following amides are prepared using a similar procedure.

2-(8-bromo-3-iodo-quinolinyl-6-oxy)-2-methylthio-N-(2-methylbut-3-yn-2-yl) acetamide (Compound No 1 of Table 5 and No 18 of Table 7), 2-(8-bromo 3-iodo-quinolinyl-6-oxy)-2-methylthio-N-(5-methoxy-2-methylpent-3-yn-2-yl) acetamide (Compound No 20 of Table 5 and No 20 of Table 7).

EXAMPLE 5

This Example illustrates the preparation of 2-(3,8-diiodo-quinolinyl-6-oxy)-2-methylthio-N-(5-methoxy-2-methylpent-3-yn-2-yl) acetamide (Compound No 20 of Table 5 and No 23 of Table 7).

Step 1: Preparation of 3,8-diiodo-6-hydroxyquinoline

In a similar procedure to Step 2 of Example 1 3,8-dibromo-6-hydroxyquinoline (preparation described in WO 2004/108663) (6.0 g) is treated with sodium iodide, copper iodide and N,N'-dimethyl-ethane-1,2-diamine in dioxane in a sealed tube under argon, at 120° C. for 2 days. Upon cooling the mixture is treated with aqueous ammonia followed by aqueous hydrochloric (to pH 5). Extraction with ethyl acetate, drying of the organic phase over magnesium sulphate, filtration and evaporation under reduced pressure gives 3,8-diiodo-6-hydroxyquinoline which is used as such in the next step. $^1$H NMR (DMSO-d$_6$) δ ppm: 10.40 (1H, br s); 8.80 (1H, d); 8.60 (1H, d); 7.90 (1H, d); 7.10 (1H, d). (M+1)$^+$: 398.

The procedures of example 1, steps 3 to 5 is repeated using 3,8-diiodo-6-hydroxyquinoline from Step 1 above as a starting material to provide 2-(3,8-diiodo-quinolinyl-6-oxy)-2-methylthio-N-(5-methoxy-2-methylpent-3-yn-2-yl) acetamide (Compound No 20 of Table 5 and No 23 of Table 7). $^1$H NMR (CDCl$_3$) δ ppm: 9.00 (1H, d); 8.40 (1H, d); 8.10 (1H, d); 7.15 (1H, d); 6.70 (1H, br s); 5.60 (1H, s); 4.10 (2H, s); 3.39 (3H, s); 2.20 (3H, s); 1.72 (6H, s). (M+1)$^+$: 611.

The following amides are prepared using a similar procedure.

2-(3,8-diiodo-quinolinyl-6-oxy)-2-methylthio-N-(2-methyl-but-3-yn-2-yl) acetamide (Compound No 1 of Table 6 and No 21 of Table 7), 2-(3,8-diiodo-quinolinyl-6-oxy)-2-methylthio-N-(2-methyl-pent-3-yn-2-yl) acetamide (Compound No 2 of Table 5 and No 22 of Table 7).

TABLE 7

This table gives characterising data (NMR, melting point or refractive index data) for compounds that have been prepared and are in part listed in Tables 1-6.

| Cpd. No. | V | R1 | R3 | R4 | R5 | Data |
|---|---|---|---|---|---|---|
| 1 | H | CH$_3$ | CH$_3$ | CH$_3$ | H | $^1$H NMR (CDCl$_3$) δ ppm: 8.95 (1H, d); 8.45 (1H, d); 8.05 (1H, d); 7.45 (1H, dd); 7.15 (1H, d); 6.70 (1H, br s); 5.62 (1H, s); 2.40 (1H, s); 2.20 (3H, s); 1.72 (6H, s). (M + 1)$^+$: 441 |
| 2 | H | CH$_3$ | CH$_3$ | CH$_3$ | CH$_3$ | $^1$H NMR (CDCl$_3$) δ ppm: 8.95 (1H, d); 8.45 (1H, d); 8.03 (1H, d); 7.47 (1H, dd); 7.13 (1H, d); 6.70 (1H, br s); 5.60 (1H, s); 2.20 (3H, s); 1.81 (3H, s); 1.70 (3H, s); 1.69 (3H, s). (M + 1)$^+$: 455 |
| 3 | H | CH$_3$ | CH$_3$ | CH$_3$ | CH$_2$OCH$_3$ | $^1$H NMR (CDCl$_3$) δ ppm: 8.95 (1H, d); 8.47 (1H, d); 8.02 (1H, d); 7.48 (1H, dd); 7.14 (1H, d); 6.72 (1H, br s); 5.61 (1H, s); 4.11 (2H, s); 3.38 (3H, s); 2.20 (3H, s); 1.72 (6H, s). (M + 1)$^+$: 485 |
| 4 | H | CH$_3$ | CH$_3$ | CH$_3$ | CH$_2$CH$_2$OCH$_3$ | $^1$H NMR (CDCl$_3$) δ ppm: 8.93 (1H, d); 8.48 (1H, d); 8.01 (1H, d); 7.47 (1H, dd); 7.15 (1H, d); 6.72 (1H, br s); 5.61 (1H, s); 3.50 (2H, t); 3.35 (3H, s); 2.49 (2H, t); 2.20 (3H, s); 1.70 (3H, s); 1.69 (3H, s). (M + 1)$^+$: 499 |
| 5 | H | CH$_3$ | CH$_3$ | CH$_3$ | CH$_2$CH$_3$ | Mp: 140-142° C.; (M + 1)$^+$: 469 |
| 6 | H | CH$_3$ | CH$_3$ | CH$_2$CH$_3$ | H | Mp: 154-155° C.; (M + 1)$^+$: 455 |
| 7 | H | CH$_3$ | CH$_3$ | CH$_2$CH$_3$ | CH$_3$ | $^1$H NMR (CDCl$_3$) δ ppm: 8.95 (1H, d); 8.48 (1H, d); 8.04 (1H, d); 7.48 (1H, dd); 7.12 (1H, d); 6.60 (1H, br s); 5.60 (1H, s, isomer A); 5.58 (1H, s, isomer B); 2.10 (3H, s); 2.2-2.1 (2H, m); 1.88-1.78 (2H, m); 1.74 (3H, s, isomer A); 1.73 (3H, s, isomerB); 1.56 (3H, s, isomer A); 1.53 (3H, s, isomer B); 1.1 (3H, t, isomer B); 0.97 (3H, t, isomer A). (M + 1)$^+$: 469 |
| 8 | CH$_3$ | CH$_3$ | CH$_3$ | CH$_3$ | H | $^1$H NMR (CDCl$_3$) δ ppm: 8.95 (1H, d); 8.40 (1H, d); 7.30 (1H, d); 6.98 (1H, d); 6.70 (1H, br s); 5.60 (1H, s); 2.75 (3H, s); 2.40 (1H, s); 2.20 (3H, s); 1.71 (6H, s). (M + 1)$^+$: 455. Mp: 160-162° C.; |
| 9 | CH$_3$ | CH$_3$ | CH$_3$ | CH$_3$ | CH$_3$ | $^1$H NMR (CDCl$_3$) δ ppm: 8.93 (1H, d); 8.41 (1H, d); 7.30 (1H, d); 6.97 (1H, d); 6.70 (1H, br s); 5.60 (1H, s); 2.75 (3H, s); |

TABLE 7-continued

This table gives characterising data (NMR, melting point or refractive index data) for compounds that have been prepared and are in part listed in Tables 1-6.

| Cpd. No. | V | R1 | R3 | R4 | R5 | Data |
|---|---|---|---|---|---|---|
| | | | | | | 2.20 (3H, s); 1.82 (3H, s); 1.70 (3H, s); 1.68 (3H, s). $(M + 1)^+$: 469 |
| 10 | $CH_3$ | $CH_3$ | $CH_3$ | $CH_3$ | $CH_2OCH_3$ | $^1$H NMR (CDCl$_3$) δ ppm: 8.95 (1H, d); 8.40 (1H, d); 7.30 (1H, d); 6.98 (1H, d); 6.70 (1H, br s); 5.60 (1H, s); 4.11 (2H, s); 3.38 (3H, s); 2.75 (3H, s); 2.20 (3H, s); 1.72 (6H, s). $(M + 1)^+$: 499. Mp: 160-162° C.; |
| 11 | $CH_3$ | $CH_3$ | $CH_3$ | $CH_3$ | $CH_2CH_2OCH_3$ | $^1$H NMR (CDCl$_3$) δ ppm: 8.92 (1H, d); 8.40 (1H, d); 7.30 (1H, d); 6.97 (1H, d); 6.72 (1H, br s); 5.60 (1H, s); 3.48 (2H, t); 3.35 (3H, s); 2.48 (2H, t); 2.20 (3H, s); 1.70 (3H, s); 1.69 (3H, s). $(M + 1)^+$: 513 |
| 12 | $CH_3$ | $CH_3$ | $CH_3$ | $CH_3$ | $CH_2CH_3$ | $^1$H NMR (CDCl$_3$) δ ppm: 8.92 (1H, d); 8.40 (1H, d); 7.30 (1H, d); 6.98 (1H, d); 6.70 (1H, br s); 5.60 (1H, s); 2.75 (3H, s); 2.20 (3H, s); 2.18 (2H, q); 1.70 (3H, s); 1.69 (3H, s); 1.12 (3H, t). $(M + 1)^+$: 483 513 |
| 13 | $CH_3$ | $CH_3$ | $CH_3$ | CH2CH3 | H | Mp: 127-128° C.; $(M + 1)^+$: 469 |
| 14 | $CH_3$ | $CH_3$ | $CH_3$ | CH2CH3 | $CH_3$ | Mp: 96-97° C.; $(M + 1)^+$: 483 |
| 15 | Cl | CH3 | CH3 | CH3 | H | Mp: 167-169° C.; $(M + 1)^+$: 475 |
| 16 | Cl | CH3 | CH3 | CH3 | $CH_3$ | Mp: 150-151° C.; $(M + 1)^+$: 489 |
| 17 | Cl | $CH_3$ | $CH_3$ | $CH_3$ | $CH_2OCH_3$ | $^1$H NMR (CDCl$_3$) δ ppm: 9.04 (1H, d); 8.50 (1H, d); 7.62 (1H, d); 7.10 (1H, d); 6.70 (1H, br s); 5.60 (1H, s); 4.12 (2H, s); 3.38 (3H, s); 2.20 (3H, s); 1.73 (6H, s). $(M + 1)^+$: 519 |
| 18 | Br | $CH_3$ | $CH_3$ | $CH_3$ | H | Mp: 112-114° C. |
| 19 | Br | $CH_3$ | $CH_3$ | $CH_3$ | $CH_3$ | $^1$H NMR (CDCl$_3$) δ ppm: 9.02 (1H, d); 8.48 (1H, d); 7.82 (1H, d); 7.12 (1H, d); 6.70 (1H, br s); 5.60 (1H, s); 2.20 (3H, s); 1.80 (3H, s); 1.70 (3H, s); 1.69 (3H, s). Mp: 161-162° C.; $(M + 1)^+$: 533-535 |
| 20 | Br | $CH_3$ | $CH_3$ | $CH_3$ | $CH_2OCH_3$ | Mp: 161-162° C.; $(M + 1)^+$: 563-565 |
| 21 | I | $CH_3$ | $CH_3$ | $CH_3$ | H | Mp: 144-145.5° C.; $(M + 1)^+$: 567 |
| 22 | I | $CH_3$ | $CH_3$ | $CH_3$ | $CH_3$ | Mp: 68-70° C.; $(M + 1)^+$: 581 |
| 23 | I | $CH_3$ | $CH_3$ | $CH_3$ | $CH_2OCH_3$ | $^1$H NMR (CDCl$_3$) δ ppm: 9.00 (1H, d); 8.40 (1H, d); 8.10 (1H, d); 7.15 (1H, d); 6.70 (1H, br s); 5.60 (1H, s); 4.10 (2H, s); 3.39 (3H, s); 2.20 (3H, s); 1.72 (6H, s). $(M + 1)^+$: 611 |
| 24 | I | $CH_3$ | $CH_3$ | $CH_3$ | $CH_2CH_2OCH_3$ | $^1$H NMR (CDCl$_3$) δ ppm: 8.98 (1H, d); 8.40 (1H, d); 8.10 (1H, d); 7.16 (1H, d); 6.70 (1H, br s); 5.60 (1H, s); 3.49 (2H, t); 3.36 (3H, s); 2.48 (2H, t); 2.20 (3H, s); 1.70 (3H, s); 1.69 (3H, s). $(M + 1)^+$: 625 |
| 25 | I | $CH_3$ | $CH_3$ | $CH_3$ | $CH_2CH_3$ | $^1$H NMR (CDCl$_3$) δ ppm: 9.00 (1H, d); 8.40 (1H, d); 8.10 (1H, d); 7.15 (1H, d); 6.72 (1H, br s); |

TABLE 7-continued

This table gives characterising data (NMR, melting point or refractive index data) for compounds that have been prepared and are in part listed in Tables 1-6.

| Cpd. No. | V | R1 | R3 | R4 | R5 | Data |
|---|---|---|---|---|---|---|
| | | | | | | 5.62 (1H, s); 2.20 (3H, s); 2.18 (2H, q); 1.70 (3H, s); 1.68 (3H, s); 1.11 (3H, t). $(M + 1)^+$: 595 |
| 26 | I | $CH_3$ | $CH_3$ | $CH_3$ | $CH_2OCH_2CH_3$ | Mp: 138-139° C.; $(M + 1)^+$: 625 |
| 27 | I | $CH_3$ | $CH_3$ | $CH_3$ | $CH_2OCH_2CHCH_2$ | $^1$H NMR (CDCl$_3$) δ ppm: 9.00 (1H, d); 8.40 (1H, d); 8.10 (1H, d); 7.18 (1H, d); 6.70 (1H, br s); 5.98-5.88 (1H, m); 5.60 (1H, s); 5.32 (1H, dd); 5.22 (1H, dd); 4.20 (2H, s); 4.05 (2H, dt); 2.20 (3H, s); 1.73 (6H, s). $(M + 1)^+$: 637 |
| 28 | Cl | $CH_3$ | $CH_3$ | $CH_3$ | $CH_2CH_3$ | $^1$H NMR (CDCl$_3$) δ ppm: 9.03 (1H, d); 8.47 (1H, d); 7.61 (1H, d); 7.08 (1H, d); 6.62 (1H, br s); 5.57 (1H, s); 2.19 (3H, s); 2.24-2.11 (2H, m); 1.69 (3H, s); 1.68 (3H, s); 1.11 (3H, t). $(M + 1)^+$: 503 |
| 29 | Cl | $CH_3$ | $CH_3$ | $CH_3$ | $CH_2OCH_2CH_3$ | $^1$H NMR (CDCl$_3$) δ ppm: 9.02 (1H, d); 8.47 (1H, d); 7.60 (1H, d); 7.07 (1H, d); 6.65 (1H, br s); 5.58 (1H, s); 4.14 (2H, s); 3.60-3.48 (2H, m); 2.18 (3H, s); 1.71 (6H, s); 1.21 (3H, t). $(M + 1)^+$: 533 |
| 30 | Cl | $CH_3$ | $CH_3$ | $CH_3$ | $CH_2OCH_2CCH$ | $^1$H NMR (CDCl$_3$) δ ppm: 9.03 (1H, d); 8.49 (1H, d); 7.61 (1H, d); 7.07 (1H, d); 6.63 (1H, br s); 5.59 (1H, s); 4.29-4.19 (4H, m); 2.43 (1H, t); 2.19 (3H, s); 1.71 (6H, s). $(M + 1)^+$: 543 |
| 31 | Cl | $CH_3$ | $CH_3$ | $CH_3$ | $CH_2OCH_2CHCH_2$ | $^1$H NMR (CDCl$_3$) δ ppm: 9.03 (1H, d); 8.47 (1H, d); 7.61 (1H, d); 7.08 (1H, d); 6.65 (1H, br s); 5.94-5.84 (1H, m); 5.58 (1H, s); 5.30 (1H, m); 5.21 (1H, m); 4.16 (2H, s), 4.05-4.04 (2H, m); 2.18 (3H, s); 1.71 (6H, s). $(M + 1)^+$: 545 |
| 32 | H | $CH_3$ | $CH_3$ | $CH_3$ | $CH_2OCH_2CCH$ | $^1$H NMR (CDCl$_3$) δ ppm: 8.91 (1H, d); 8.44 (1H, d); 8.00 (1H, dd); 7.43 (1H, dd); 7.13 (1H, d); 6.71 (1H, br s); 5.61 (1H, s); 4.26 (2H, s); 4.23 (2H, d); 2.43 (1H, t); 2.18 (3H, s); 1.70 (6H, s). $(M + 1)^+$: 509 |
| 33 | H | $CH_3$ | $CH_3$ | $CH_3$ | $CH_2OCH_2CHCH_2$ | $^1$H NMR (CDCl$_3$) δ ppm: 8.91 (1H, d); 8.43 (1H, d); 7.99 (1H, dd); 7.42 (1H, dd); 7.13 (1H, d); 6.72 (1H, br s); 5.92-5.82 (1H, m); 5.60 (1H, s); 5.28 (1H, m); 5.18 (1H, m); 4.14 (2H, s), 4.03-4.02 (2H, m); 2.17 (3H, s); 1.70 (6H, s). $(M + 1)^+$: 511 |
| 34 | H | $CH_3$ | $CH_3$ | $CH_3$ | $CH_2OCH_2CH_3$ | $^1$H NMR (CDCl$_3$) δ ppm: 8.92 (1H, d); 8.45 (1H, d); 8.01 (1H, dd); 7.44 (1H, dd); 7.13 (1H, d); 6.72 (1H, br s); 5.60 (1H, s); 4.14 (2H, s); 3.60-3.50 (2H, m); 2.18 (3H, s); 1.71 (6H, s); 1.20 (3H, t). $(M + 1)^+$: 499 |

EXAMPLE 6

This Example illustrates the fungicidal properties of compounds of formula (1).

The compounds are tested in a leaf disk assay, with methods described below. The test compounds are dissolved in DMSO and diluted into water to 200 ppm. In the case of the test on *Pythium ultimum*, they are dissolved in DMSO and diluted into water to 20 ppm. *Eysiphe graminis* f.sp. *tritici* (wheat powdery mildew): Wheat leaf segments are placed on agar in a 24-well plate and sprayed with a solution of the test compound. After allowing to dry completely, for between 12 and 24 hours, the leaf disks are inoculated with a spore suspension of the fungus. After appropriate incubation the activity of a compound is assessed four days after inoculation as preventive fungicidal activity.

*Puccinia recondita* f.sp. *tritici* (wheat brown rust): Wheat leaf segments are placed on agar in a 24-well plate and sprayed with a solution of the test compound. After allowing to dry completely, for between 12 and 24 hours, the leaf disks are inoculated with a spore suspension of the fungus. After appropriate incubation the activity of a compound is assessed nine days after inoculation as preventive fungicidal activity.

*Septoria nodorum* (wheat glume blotch): Wheat leaf segments are placed on agar in a 24-well plate and sprayed with a solution of the test compound. After allowing to dry completely, for between 12 and 24 hours, the leaf disks are inoculated with a spore suspension of the fungus. After appropriate incubation the activity of a compound is assessed four days after inoculation as preventive fungicidal activity.

*Pyrenophora teres* (barley net blotch): Barley leaf segments are placed on agar in a 24-well plate and sprayed with a solution of the test compound. After allowing to dry completely, for between 12 and 24 hours, the leaf disks are inoculated with a spore suspension of the fungus. After appropriate incubation the activity of a compound is assessed four days after inoculation as preventive fungicidal activity.

*Pyricularia oryzae* (rice blast): Rice leaf segments are placed on agar in a 24-well plate and sprayed with a solution of the test compound. After allowing to dry completely, for between 12 and 24 hours, the leaf disks are inoculated with a spore suspension of the fungus. After appropriate incubation the activity of a compound is assessed four days after inoculation as preventive fungicidal activity.

*Botrytis cinerea* (grey mould): Bean leaf disks are placed on agar in a 24-well plate and sprayed with a solution of the test compound. After allowing to dry completely, for between 12 and 24 hours, the leaf disks are inoculated with a spore suspension of the fungus. After appropriate incubation the activity of a compound is assessed four days after inoculation as preventive fungicidal activity.

*Phytophthora infestans* (late blight of potato on tomato): Tomato leaf disks are placed on water agar in a 24-well plate and sprayed with a solution of the test compound. After allowing to dry completely, for between 12 and 24 hours, the leaf disks are inoculated with a spore suspension of the fungus. After appropriate incubation the activity of a compound is assessed four days after inoculation as preventive fungicidal activity.

*Plasmopara viticola* (downy mildew of grapevine): Grapevine leaf disks are placed on agar in a 24-well plate and sprayed a solution of the test compound. After allowing to dry completely, for between 12 and 24 hours, the leaf disks are inoculated with a spore suspension of the fungus. After appropriate incubation the activity of a compound is assessed seven days after inoculation as preventive fungicidal activity.

*Pythium ultimum* (Damping off): Mycelial fragments of the fungus, prepared from a fresh liquid culture, are mixed into potato dextrose broth. A solution of the test compound in dimethyl sulphoxide is diluted with water to 20 ppm then placed into a 96-well microtiter plate and the nutrient broth containing the fungal spores is added. The test plate is incubated at 24° C. and the inhibition of growth is determined photometrically after 48 hours.

The following compounds (number of compound first, followed by table number in brackets) gives at least 60% control of the following fungal infection at 200 ppm:

*Plasmopara viticola*, compounds 1(4), 2(4), 20(4), 1(6), 20(6), 1(1), 2(1), 3(1), 21(1), 20(1), 1(2), 2(2), 3(2), 21(2), 20(2), 6(7), 7(7), 13(7), 14(7), 28(7), 29(7), 30(7), 31(7), 32(7), 33(7), 34(7).

*Phytophthora infestans*, compounds 1(5), 2(5), 20(5), 1(4), 2(4), 20(4), 20(6), 1(1), 2(1), 3(1), 21(1), 20(1), 1(2), 2(2), 3(2), 21(2), 20(2), 6(7), 7(7), 13(7), 14(7), 28(7), 29(7), 30(7), 31(7), 32(7), 33(7), 34(7).

*Erysiphe graminis* f.sp. *tritici*, compounds 1(5), 2(5), 20(5), 1(4), 1(6), 20(6), 1(1), 2(1), 3(1), 21(1), 20(1), 6(7), 7(7), 13(7), 1(2), 2(2), 20(2), 28(7), 29(7), 30(7), 31(7), 32(7), 33(7), 34(7).

*Pyricularia otyzae*, compounds 1(5), 1(4), 1(2), 21(2), 13(7), 6(7), 1(1), 2(1), 20(1).

*Botrytis cinerea*, compounds 20(5), 3(2), 2(1), 7(7).

*Pyrenophora teres*, compounds 1(5), 1(2).

*Puccinia recondita* f.sp. *tritici*, compounds 1(5), 1(4), 20(4), 1(6), 2(6), 1(2), 2(2), 3(2), 1(1), 3(1), 13(7), 6(7), 32(7), 33(7), 34(7).

*Septoria nodorum*, compound 1(5), 2(5), 20(5), 1(4), 2(4), 20(4), 1(6), 2(6), 20(6), 1(1), 2(1), 3(1), 21(1), 20(1), 1(2), 2(2), 3(2), 21(2), 20(2), 6(7), 7(7), 13(7), 14(7), 28(7), 29(7), 30(7), 31(7), 32(7), 33(7), 34(7).

The following compounds (number of compound first, followed by table number in brackets) give at least 60% control of the following fungal infection at 20 ppm:

*Pythium ultimum*, compounds 1(5), 2(5), 20(5), 1(4), 1(6), 2(6), 20(6), 1(1), 2(1), 3(1), 21(1), 20(1), 1(2), 3(2), 21(2), 6(7), 7(7), 13(7), 32(7), 33(7), 34(7).

Comparison of the fungicidal activity of compound No. 19 of Table 7 according to the invention with the structurally most closely related compound from the state of the art (compound No. 2 of Table 25 described in Table 142 on page 108 of WO 2004/108663 A1.

Compound No. 19 (Table 7) according to the invention

[Chemical structure: iodo-bromo-quinoline with O-CH(SMe)-C(=O)-NH-C(CH3)2-C≡C-CH3]

Compound 2 (Table 23) according to WO 2004/108663 A1

[Chemical structure: dibromo-quinoline with O-CH(SMe)-C(=O)-NH-C(CH3)2-C≡C-CH3]

TABLE 8

Activity against *Septoria nodorum*
Description of test: Wheat leaf segments are placed on agar in a 24-well plate and sprayed with a solution of the test compound. After allowing to dry completely, for between 12 and 24 hours, the leaf disks are inoculated with a spore suspension of the fungus. After appropriate incubation the activity of a compound is assessed four days after inoculation as preventive fungicidal activity.

| Concentration (ppm) | Efficacy (%) of Compound No. 19 (Table 7) according to invention | Efficacy (%) of Compound No. 2 (Table 23) according to WO 2004/108663 |
|---|---|---|
| 200 | 100 | 0 |
| 60 | 80 | 0 |

Table 8 shows that compound Compound No. 19 of Table 7 according to the invention exerts a substantially better fungicidal activity against *Septoria nodorum* than the compound from the state of the art (Compound No, 2 of the Table 23 described on page 108 of WO 2004/108663 A1). At both application rates, the compound according to the invention is far superior to the compound of the state of the art. This enhanced effect was surprising in view of the structural similarity of these compounds.

The invention claimed is:

1. A compound of the general formula (1):

[Chemical structure (1): Ar-O-CH(S(O)nR1)-C(=O)-NH-C(R3)(R4)-C≡C-R5]

wherein Ar is a group of the formula (A):

[Chemical structure (A): iodo-methyl-V-quinoline]

wherein

V is H, halogen or methyl, $R^1$ is methyl or ethyl, $R^3$ and $R^4$ are independently H, $C_{1-3}$ alkyl, $C_{2-3}$ alkenyl or $C_{2-3}$ alkynyl, or $R^3$ and $R^4$ join with the carbon atom to which they are attached to form a 4 or 5-membered carbocyclic ring optionally containing one O, S or N atom and optionally substituted with halogen or $C_{1-4}$ alkyl, $R^5$ is H, $C_{1-4}$ alkyl or $C_{3-6}$ cycloalkyl or $C_{3-6}$ cycloalkoxy or $C_{2-4}$ alkenyl, in which the alkyl or cycloalkyl or cycloalkoxy or alkenyl group is optionally substituted with halogen, hydroxy, $C_{1-6}$ alkoxy, $C_{1-4}$ alkoxy-$C_{1-4}$ alkoxy, cyano, $C_{3-5}$ alkenyloxy or $C_{3-5}$ alkynyloxy, and n is 0, 1 or 2.

2. A compound according to claim 1, wherein V is H, chloro, bromo or methyl.

3. A compound according to claim 2, wherein V is H.

4. A compound according to claim 1, wherein $R^3$ and $R^4$ are independently H or $C_{1-3}$ alkyl or $R^3$ and $R^4$ join with the carbon atom to which they are attached to form a 4 or 5-membered carbocyclic ring.

5. A compound according to claim 1, wherein $R^5$ is H, $C_{1-4}$ alkyl, $C_{3-6}$ cycloalkyl, $C_{1-6}$ alkoxy-$C_{1-4}$ alkyl, $C_{3-6}$ alkenyloxy-$C_{1-4}$ alkyl, $C_{3-6}$ alkynyloxy-$C_{1-4}$ alkyl, $C_{1-4}$ hydroxyalkyl, or $C_{1-4}$ haloalkyl.

6. A compound according to claim 1, wherein V is H, chloro, bromo or methyl, $R^1$ is methyl, n is 0, $R^3$ and $R^4$ are independently $C_{1-3}$ alkyl and $R^5$ is H, $C_{1-4}$ alkyl or $C_{1-4}$ alkyl substituted with hydroxy, $C_{1-6}$ alkoxy, $C_{3-4}$ alkenyloxy or $C_{3-4}$ alkynyloxy.

7. A compound according to claim 6, wherein V is H, chloro, bromo or methyl, $R^1$ is methyl, n is 0, $R^3$ and $R^4$ are methyl and $R^5$ is $CH_2OH$, $CH_2OMe$, $CH_2OEt$, $CH_2OCH_2CHCH_2$, $CH_2OCH_2CCH$, $(CH_2)_2OMe$.

8. A process for preparing a compound of the formula (1) according to claim 1, wherein n is 0, which comprises reacting a compound of the formula

[Chemical structure (7): Ar-O-CH(SR1)-C(=O)-OH]

wherein Ar and R¹ are as defined in claim 1, with a compound of the formula

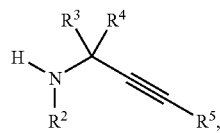
(8)

wherein R² is hydrogen and R³, R⁴ and R⁵ are as defined in claim 1.

9. A process for preparing a compound of the formula (1) according to claim 1, wherein n is 0, which comprises reacting a compound of the formula (16)

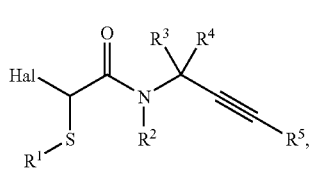
(16)

wherein R¹, R³ to R⁵ are as defined in claim 1, R² is hydrogen and Hal is halogen, with a compound ArOH, wherein Ar is as defined in claim 1.

10. A process for preparing a compound of the formula (25a)

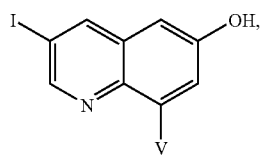
(25a)

wherein V is as defined in claim 1, which comprises reacting a compound of the formula (25)

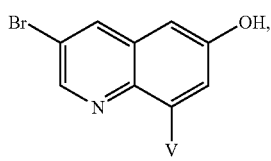
(25)

with a catalytic amount of a copper salt in the presence of a metal iodide and a N,N-dialkylethylenediamine ligand.

11. A process for preparing a compound of the formula (27)

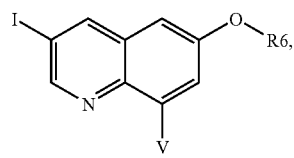
(27)

wherein V is as defined in claim 1 and R⁶ is an alkyl group, which comprises reacting a compound of the formula (26)

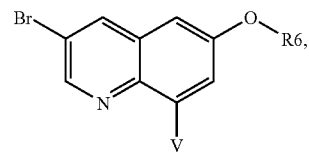
(26)

with a catalytic amount of a copper salt in the presence of a metal iodide and a N,N-dialkylethylenediamine ligand.

12. A process for preparing a compound of the formula (29)

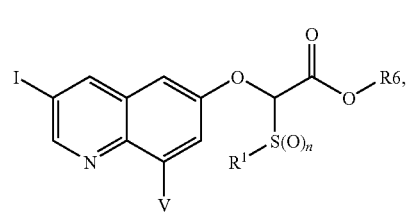
(29)

wherein V, n and R¹ are as defined in claim 1 and R⁶ is an alkyl group, which comprises reacting a compound of the formula (28)

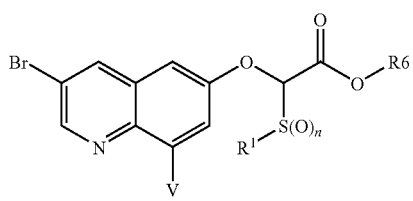
(28)

with a catalytic amount of a copper salt in the presence of a metal iodide and a N,N-dialkylethylenediamine ligand.

13. A process for preparing a compound of the formula (1) according to claim 1

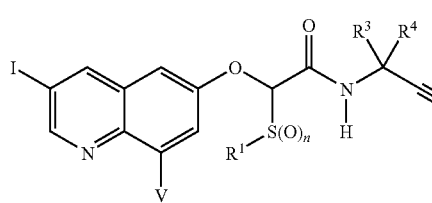
(1)

wherein V, n, $R^1$ and $R^3$ to $R^5$ are as defined in claim 1, which comprises reacting a compound of the formula (1a)

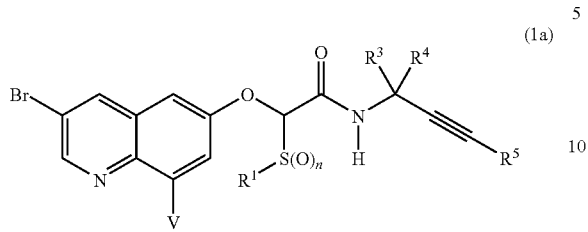

with a catalytic amount of a copper salt in the presence of a metal iodide and a N,N-dialkylethylenediamine ligand.

14. A fungicidal composition comprising a fungicidally effective amount of a compound of formula (1) according to claim 1 and a suitable carrier or diluent.

15. A method of combating or controlling phytopathogenic fungi which comprises applying a fungicidally effective amount of a compound of formula (1) according to claim 1.

\* \* \* \* \*